(12) United States Patent
Kumagai et al.

(10) Patent No.: US 6,872,709 B2
(45) Date of Patent: Mar. 29, 2005

(54) THERAPEUTIC AGENT FOR MASTITIS OF LIVESTOCK AND METHOD FOR TREATING MASTITIS USING THE SAME AGENT

(75) Inventors: Katsuo Kumagai, Miyagi-ken (JP); Kenzo Kai, Miyagi-ken (JP); Ken-ichi Komine, Miyagi-ken (JP)

(73) Assignee: Kyoritsu Seiyaku Corporation, Tokyo (JP)

( * ) Notice: Subject to any disclaimer, the term of this patent is extended or adjusted under 35 U.S.C. 154(b) by 0 days.

(21) Appl. No.: 10/629,117

(22) Filed: Jul. 28, 2003

(65) Prior Publication Data

US 2004/0067899 A1 Apr. 8, 2004

Related U.S. Application Data

(63) Continuation of application No. 09/995,040, filed on Nov. 26, 2001, now abandoned.

(30) Foreign Application Priority Data

Nov. 24, 2000 (JP) .................................... P2000-358055
Feb. 22, 2001 (JP) .................................... P2001-046565

(51) Int. Cl.$^7$ ....................... A61K 31/704; C07H 15/20
(52) U.S. Cl. .......................................... 514/33; 536/4.1
(58) Field of Search .............................. 514/33; 536/4.1

(56) References Cited

U.S. PATENT DOCUMENTS 4,678,772 A * 7/1987 Segal et al. .................... 514/25

FOREIGN PATENT DOCUMENTS

| GB | 798655 | 3/1957 | | |
| GB | 799415 | 3/1957 | | |
| GB | 843135 | 6/1958 | | |
| JP | 172332 | * | 7/1989 | .......... A61K/35/76 |
| JP | 06-305932 | 11/1994 | | |

OTHER PUBLICATIONS

Nagai et al., Japan J. Pharmacol. 1992, 58, 209–218.*

Fujisawa, Yumiko, et al., "Glycyrrhizin Inhibits the Lytic Pathway of Complement–Possible Mechanism of Its Anti-Inflammatory Effect on Liver Cells in Viral Hepatitis," *Microbiol. Immunol.*, vol. 44, No. 9, pp. 799–804 (2000).

Fukai, Toshio, et al., "Cytotoxic Activity of Low Molecular Weight Polyphenols against Human Oral Tumor Cell Lines," *Anticancer Research*, vol. 20, pp. 2525–2536 (2000).

Jeong, H., et al., Induction of Inducible Nitric Oxide Synthase Expression by 18β–glycyrrhetinic Acid in Macrophages, *FEBS Letters*, vol. 513., pp. 208–212 (2002).

Kai, Kenzo, et al., Anti–inflammatory effects of Intrammamary Infusions of Glycyrrhizin in Lactating Cows with Mastitis Caused by Coagulase–negative Staphylococci, *AJVR*, vol. 64, No. 10, pp. 1213–1220 (2003).

Mishima, Mathiro et al., "Studies on glycyrrhetinate and its derivatives as nasal absorption promoter of insulin," *Drug Delivery System*, p. 88, 1989, issue 4.

Okada, Kenzo, et al., Identification of Antimicrobial and Antioxidant Constituents from Licorice of Rusian and Xhijiang Origin, *Chem. Pharm. Bull.*, vol. 37, No. 9, pp. 2528–2530 (1989).

Sakagami, H., et al., "Induction of Apoptosis by Flavones, Flavonols (3–Hydroxyflavones) and Isoprenoid–Substituted Flavonoids in Human Oral Tumor Cell Lines", *Anticancer Research*, vol. 20, pp. 271–278 (2000).

Suzuki, H., et al., "Effects of Glycyrrhizin on Biochemical Tests in Patients with Chronic Hepatitis," *Asian Med. J.*, vol. 26, No. 7, pp. 423–438.

Utsunomiya, Tokuichiro et al., "Glycyrrhizin (20 β–carboxy–11–oxo–30–norolean–12–en–3β–yl–2–O–β–D–glucopyranuronosyl–α–D–glucopyranosiduronic acid) improves the resistance of thermally injured mice to opportunistic infection of herpes simplex virus type 1," *Immunology Letters*, vol. 44, pp. 59–66 (1995).

* cited by examiner

*Primary Examiner*—James O. Wilson
*Assistant Examiner*—Ganapathy Krishnan
(74) *Attorney, Agent, or Firm*—Kilpatrick Stockton LLP

(57) ABSTRACT

The present invention provides a therapeutic agent and therapeutic method for treatment of mastitis in livestock comprising glycyrrhizin and pharmaceutically acceptable salts thereof as effective ingredients.

7 Claims, No Drawings

THERAPEUTIC AGENT FOR MASTITIS OF LIVESTOCK AND METHOD FOR TREATING MASTITIS USING THE SAME AGENT

RELATED APPLICATIONS

This application is a continuation of U.S. patent application Ser. No. 09/995,040, filed Nov. 26, 2001, now abandoned.

BACKGROUND OF THE INVENTION

1. Field of the Invention

The present invention relates to a therapeutic agent for the treatment of mastitis in livestock, and a method for treating mastitis using the same. Particularly, the present invention relates to a therapeutic agent and method for the treatment of mastitis in livestock during lactation periods.

2. Description of the Related Art

Mammals described as livestock, for example, cattle, horses, goats, sheep, pigs and rabbits, all possess a mammary gland and therefore may develop mastitis. Livestock that are frequently milked, for example, cattle and in particular the milk cow, are most liable to develop mastitis. Mastitis is one of the most difficult diseases to cure for the milk cow. Mastitis tends occur more frequently in recent years due to milking stress as a result of large scale breeding of cows and wide spread use of milking machines. Consequently, the mammae of cows often develop mastitis, with an incidence of as high as ¼ of the total milk cows, including subclinical cows.

It has been reported that the number of somatic cells in cow's milk increases with the development of mastitis, and the disease adversely affects the quality and flavor of the dairy products. The number of the somatic cells (referred to as somatic cell counts, SCC hereinafter) in the raw milk of a healthy cow is 500,000 cells/mL or less. In contrast, SCC in the raw milk of a cow with mastitis reportedly increases to 1,600,000 cells/mL or more. According to statistical studies, the milk production of the cow decreases by 0.4 kg a day and 0.6 kg a day in primipara cow and multipara cow, respectively, for every increase of twice as much as SCC of 50,000 cells/mL or less. The fat content of the raw milk is also reported to decrease at a rate of 0.2 g/kg for every increase of twice as much as SCC (Am. J. Vet. Res., vol. 29, 497, 1968).

Naturally, distribution of the milk collected from cows infected with mastitis is suspended. Accordingly, economic losses caused by this disease are substantial.

Mastitis is a highly intractable disease, firstly because it is induced by a variety of microorganisms. Representative causative microorganisms include *Staphylococcus aureus, Streptococcus agalaotiae, Streptococcus dysgalactias, Escherichia coli* and *Corynebacterium pyogenes*. Infection by these microorganisms, is triggered by the stress such as large-scale breeding and wide spread use of the milking machines on the cow. Therefore, the number of infected cow Is increasing each year.

A second reason for the intractability of mastitis is that because it is considered along with other microbial diseases, and protection from mastitis relies too much on the use of highly potent antibiotics. Too much reliance on the antibiotics tends to neglect the importance of studies of pathological mechanisms of the onset of the disease and chronic infection mechanisms. It has been common means of treatment to select from and inject antibacterial agents such as furan and sulfur agents and antibiotics such as penicillin, sefem, streptomycin, tetracycline and macrolide based antibiotics.

However, these antibacterial substances may affect human health because the resistant bacteria occur due to residual antibacterial substances in the milk. Consequently, the period of use of these antibacterial substances is strictly restricted. Use of these antibacterial substances is also strictly restricted worldwide by a variety of regulations. Therefore, medication is often forced to be interrupted, even before sufficient remedial effects are achieved. As a result, dairy farmers are often troubled by recurrence of the disease and within a short time have to resume of medication.

A third reason for the intractability of mastitis is that the immune system of the mammary gland of milk cow differs according to the secretion and non-secretion periods of the milk secretion cycle (Vet. Immunol. & Immunopathol., vol. 65, 51–61, 1998; J. Diary Sci., vol. 82, 1459–1464, 1999). This may in fact be the main cause of the intractability of mastitis. That is, the modes of microbial infection in the mammary gland tissue are different, and infection protection mechanisms of the mammary gland itself may be very different during these periods.

During the active secretion period of as long as 10 months, the cells in the mammary gland and the immune system in the secreted milk is mainly composed of $CD8'T$-cells and $\gamma\delta'T$-cells that by themselves control epithelium cells concerning secretion of the milk. Accordingly, the immune function during this milk secretion period mainly operates by the cell-mediated immunity of Th1 (a group of helper T-cells).

The cells in the mammary gland and milk during the non-secretion dry period are mainly composed of leukocytes, $CD4'T$-cells and B cells originating from the blood and spinal cord. Accordingly, the immune function mainly operates by phagocytic response and humoral immunity mainly comprising antibodies and complements.

In other words, both periods involve quite contrasting immune mechanisms, and perform quite contrasting methods of protection against infection. Therefore, measures for protecting the animal from infection should naturally be different according to these periods. However, these features have not been taken into consideration in conventional countermeasures against infection.

Glycyrrhizin has been reported as having a variety of immunological functions in experimental animals such as mice. For example, glycyrrhizin stimulates the lymphocytes and induces production of IFN (interferon, Microbial. Immunol., vol. 26, 535–539, 1982) to enhance killer activities of the NK (natural killer) cells (Excerpta Medica International Conference Series, vol. 641, 460–464, 1983). In addition, glycyrrhizin is known to facilitate activation of the extra-thymus differentiated T-cells including $\gamma\delta'T$-cells and $CD8'T$-cells that are selectively distributed in the intestinal tract and mucosal organs independently of the thymus of the mouse (Biotherapy, vol. 5, 167–176, 1992). Otherwise, glycyrrhizin is known to facilitate a boost-up of cellular immunity based on the activation of the helper T-cells (in particular Th1 helper cells), thereby participating in protection of various virus infection diseases including retrovirus infection (Biotherapy, vol. 9, 209–220, 1996) and the suppression of allergic responses of the skin. Glycyrrhizin with protective effects against herpes virus induced death of the mucosal membrane (Immunol. Lett. vol. 44, 59–66, 1995) has also been proven to enhance immune activity with glycyrrhlzin in a mouse with immune deficiency that the skin is being burned.

The effect of glycyrrhlzin on microbial infection has been already tested on the human virus diseases, and the compound is reported to suppress viral hepatitis by oral and intravenous administration (Asian Med. J. vol. 26, 423–438, 1983; Microb. Immunol., vol. 44, 799–804, 2000).

In addition, glycyrrhizin has been used as an anti-inflammatory agent for external use on the human skin (Japanese Patent Laid-open No. 6–305932).

Further, glycyrrhizin has been used as a human nasal absorption drug as an absorption-accelerating agent (Drug Delivery System, vol. 4, 88–93, 1989).

However, although glycyrrhizin has been shown to have immunological functions in experimental animals such as a mouse and anti-inflammatory functions in humans, the idea for applying glycyrrhizin for mastitis of the livestock is unprecedented. Still more, the idea of applying glycyrrhizin to cow mastitis having complicated immune functions and caused by infection of various microorganisms is, too, unprecedented.

SUMMARY OF THE INVENTION

Accordingly, it is an object of the present invention to provide a therapeutic agent and a therapeutic method for the treatment of mastitis in livestock.

More particularly, it is another object of the present invention to provide a therapeutic agent against mastitis during the milk secretion period of the livestock.

The present invention provides a therapeutic agent against mastitis in livestock, comprising glycyrrhizin or the pharmaceutically acceptable salts thereof as effective ingredients.

The present invention also provides a therapeutic agent against mastitis in livestock, comprising glycyrrhizin or the pharmaceutically acceptable salts thereof as effective ingredients for use during the milk secretion period.

The present invention further provides a therapeutic agent against mastitis in livestock, comprising administering glycyrrhizin or the pharmaceutically acceptable salts thereof into the mammae of the livestock.

The present invention further provides a therapeutic method for the treatment of mastitis in livestock, comprising directly injecting glycyrrhizin or pharmaceutically acceptable salts thereof into the mammae of the livestock.

The present invention further provides a therapeutic method for the treatment of mastitis in livestock, comprising administering glycyrrhizin or pharmaceutically acceptable salts thereof into the mammae of the livestock during the milk secretion period.

The present invention further provides a therapeutic method for the treatment of mastitis in livestock, comprising directly administering glycyrrhizin or pharmaceutically acceptable salts thereof into the mammae of the livestock during the milk secretion period.

The present invention further provides a therapeutic method for the treatment of mastitis in livestock, comprising directly injecting glycyrrhizin or pharmaceutically acceptable salts thereof into the mammae of the livestock during the milk secretion period.

The present invention further provides the therapeutic agent or therapeutic method, wherein the livestock includes cattle.

The present invention further provides a therapeutic method for mastitis comprising directly injecting glycyrrhizin or pharmaceutically acceptable salts thereof into the mammae of cattle using a cannula.

The present invention provides therapeutic agents and therapeutic methods for treating mastitis of the livestock. Particularly, the present invention provides therapeutic agents for the treatment of mastitis during the milk secretion period of livestock. In addition, using glycyrrhizin or its salt that are commonly used as a food additive for humans alleviates human safety problems.

The present disclosure relates to subject matter contained in Japanese Patent Application No. 2000-358055, filed on Nov. 24, 2000 and Japanese Patent Application No. 2001-46565, filed on Feb. 22, 2001, the disclosure of which is expressly incorporated herein by reference in its entirety.

DESCRIPTION OF THE PREFERRED EMBODIMENTS

The effective ingredient of the therapeutic agent for the treatment of mastitis according to the present invention comprises glycyrrhizin, represented by the following formula, or pharmaceutically acceptable salts thereof.

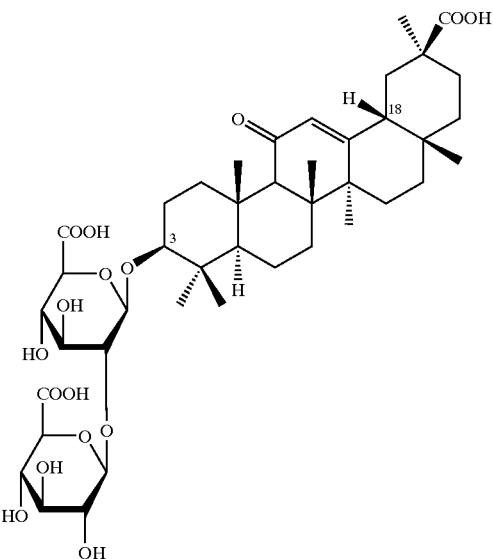

Glycyrrhizin (glycyrrhizinic acid) to be used in the present invention is obtained by extracting the root and stolon of Glycyrrhiza (Glycyrrhiza uralensis Fisher, Glycyrrhiza Giabra Linne) or plants belonging to the same genus as Glycyrrhiza (Glycyrrhiza inflata Batalin, Glycyrrhiza korshinsky G. Grig., et al.) with a glycyrrhizin soluble solvent such as water, methanol, ethanol and n-butanol. Commercially available glycyrrhizin may be used.

Pharmacologically acceptable salts include ammonium and alkali metal salts of glycyrrhizin or a choline salt of glycyrrhlzin obtained by reacting glycyrrhizin and an inorganic or organic base at a 1:1, 1:2 or 1:3 molar ratio. However, the salts are not necessarily restricted to those described above so long as the safety of the cow and the dairy farmer is ensured. Glycyrrhizin alone or any plural combination of salts thereof may be formulated as effective ingredients of the therapeutic agent.

Glycyrrhizin derivatives obtained by a conventional chemical synthesis using glycyrrhizin as a starting material may be used as the effective ingredient of the therapeutic agent, so long as they are effective for the treatment of mastitis.

Formulations containing these effective ingredients comprise an ointment in which glycyrrhlzin or its salt is uniformly dispersed in an ointment base, or a liquid preparation prepared by dissolving glycyrrhizin or its salt in water or ethanol. These formulations may be manufactured using conventional arts. A therapeutic agent containing commercially available glycyrrhizin may be used.

Examples of the ointment base to be used for preparing the ointment include, though not restrictive, hydrophobic ointment bases such as white petroleum, yellow petroleum, liquid paraffin, olive oil, peanuts oil, soybean oil and lanolin; and hydrophilic ointment bases such as polyethylene glycol, sodium polyacrylate, stearyl alcohol, stearic acid, aluminum stearate, glycerin, sodium arginate and carboxymethyl cellulose.

The solvents to be used for the liquid preparation include, though not restrictive, polypropylene glycol, polyethylene glycol and glycerin in addition to those described above.

Additives such as a buffer agent, an osmotic pressure adjustment agent, a stabilizer and an antiseptic may also be added.

Glycyrrhizin and other ingredients that will be left in the raw milk have no adverse effects on the human health, since the therapeutic agent according to the present invention contains glycyrrhizin and other ingredient that are commonly used as food additives for humans. The agent is particularly effective for the cattle during its milk secretion period.

The total dosage of glycyrrhizin and its salt is preferably 400 to 800 mg per mamma. The therapeutic agent is preferably administered to have a glycyrrhizin concentration in the milk of 0.08 to 0.4 mg/mL. These values have been determined by converting the dosage for humans into the volume of the milk in the mammae.

The agent may be administered once, twice or more a day. Or, it may be administered every few days.

The therapeutic agent is directly injected into the mammae as an ointment or liquid preparation. Such as a cannula and a syringe are used for injection, use of the cannula is preferable considering the volume being administered.

While examples of the present invention are described in detail hereinafter, the present invention is by no means restricted to these examples.

Therapeutic tests were performed in seven cases of clinical type mastitis of Holstein cow using a glycyrrhizin therapeutic agent (High Efficiency Kaneo-Minofagen C made by Minofagen Pharmaceutical Industries Co.) using the method described in the following Examples 1 to 5, 6 and 7.

EXAMPLES 1 to 5

A therapeutic composition containing glycyrrhizin shown below was dissolved into water to a final volume of 1000 mL, and its pH and osmotic pressure were adjusted to 6.7 and 2, respectively, in order to prepare a therapeutic agent of the invention. The formulation of the herapeutic composition is shown below.

The therapeutic agent containing 400 mg equivalence glycyrrhizin was administered into the mamma manifesting mastitis using a cannula on day zero of recognition of the disease. The results of treatment were evaluated on day 0, 1 t 3, 7, 14 and 21, which will be described hereinafter. These Results are Shown in Tables 1 to 5.

Formulation of the Composition Containing Glycyrrhizin Therapeutic Agent (High Efficiency Kaneo-Minofagen C)

| | |
|---|---|
| glycyrrhizin ammonium salt | 2.0 g as converted into glycyrrhizin |
| aminoacetic acid | 20.0 g |
| L-cysteine hydrochloride | 1.0 g |
| sodium chloride | 5.0 g |
| anhydrous sodium bisulfate | 0.8 g |

EXAMPLES 6 and 7

The therapeutic agents corresponding to 400 mg and 800 mg of glycyrrhizin were administered in Example 6 and 7, respectively, into the mamma manifesting mastitis on day zero and on day three after starting the tests. The method of medication and of evaluation of the treatment were the same as those described in Examples 1 to 5. These results are shown in Tables 6 and 7.

(Evaluation of the Results of Treatment)

The results of the treatment were evaluated by clinical observation and test for the milk.

Clinical observations were performed with respect to "Inflation and rigidity of the mammae" and "aggregates in the milk". The tests of the milk were performed with respect to "degree of coagulation of the milk", "Judgment by pH of the milk", "the number of somatic cells in the milk" and "the number of granulocytes in the milk". The evaluation method is described in the corresponding column.

The evaluation of "degree of coagulation of the milk" and "judgment by pH of the milk" was based on "the modified California Mastitis Test (hereinafter called CMT).

Evaluation criteria of "aggregates in the milk", "degree of coagulation of the milk" and "Judgment by pH of the milk" were employed according to "Gist of Clinical Pathology Test in Cooperative Society of Livestock, revised edition, 1997".

(Inflation and Rigidity of the Mamma)

The inflation and rigidity of the mamma were evaluated by palpation. The criteria of evaluation are as follows:

++: The mamma is totally inflated and shows severe rigidity.

+: The mamma is locally inflated and shows rigidity.

±: The mamma shows slight rigidity.

−: The mamma shows no inflation and rigidity.

(Aggregates in the Milk)

The milk was squeezed into a strip cup attached with a sheet of black n t or cloth, and the number of the aggregates was visually evaluated.

The criteria of evaluation are as follows:

++: The size and number of the aggregates are large. The number of the aggregates is three or more per mL.

+: The number of the aggregates is small, although the size is large. The number of the aggregates is 0.5 to 3 per mL.

±: The size and number of the aggregates are small. The number of the aggregates is smaller than 0.5 per mL.

−: The aggregates are not found at all.

(Degree of Coagulation of the Milk)

The degree of coagulation of the milk was Judged following the modified CMT method using a commercially available test kit (PL tester made by Nihon Zenyaku Co.). Two ml of the milk was sampled from each mamma into the plate of the test kit, and an equal volume of the modified CMT reagent was added to each plate. After gently turn the plate for one minute in order to mix the sample and reagent, the degree of coagulation was Judged.

The evaluation criteria are as follows:

+++: The milk was immediately turned into a gel, and a mass remained even after stopping to turn.

++: Although the milk immediately turned into a gel, it remained spread over the bottom of the stirrers after stopping to turn.

+: Although coagulation is evident, no gel formation was detected.

±: The milk flows smoothly irrespective of a small degree of coagulation.

−: Coagulation is not detected at all, and the raw milk flows smoothly when the plate are tilted.

(Judgment by pH of the Milk)

The pH of the milk was assessed following the evaluation criteria of the modified CMT method using the same commercially available test kit as in the coagulation test described above.

The evaluation criteria are as follows;

+++: dark green

++: green colored

+: slightly green colored

−: gold or yellow (Number of the Somatic Cells (SCC) in the Milk)

SCC was measured by allowing the cells to remain at 4° C. after mixing the milk with ethanol. The cells were stained with Propidium Iodide (PI), and the number of the positive cells was measured using FACS Calibur (Becton-Dickinson) (J. Livestock Society, vol. 70, J169–176, 1999).

(Number of the Granulocytes (PMN) in the Milk)

The number of PMN in the milk was measured using a microscope, whereby the cells were counted under a microscope by Giemsa staining after washing the milk a phosphate buffered saline (PBS) and adhering the cells to a slide glass using Cytospin (made by Shandon Scientific Ltd.) (J. Livestock Society, vol. 70, J169–176, 1999).

TABLE 1

Results of Example 1

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | + | + | ± | − | − | − |
| | Aggregates in the milk | + | + | − | − | − | − |
| Test of the milk | Degree of coagulation of the milk (modified CMT method) | ++ | ± | ± | − | − | − |
| | Judgment by pH of the milk (modified CMT method) | ± | − | − | − | − | − |
| | Number of somatic cells in the milk (SCC × 10$^4$ cells/mL) | 416 | 215 | 88 | 7 | 2 | 0.3 |
| | Number of granulocytes in the milk (PMN × 10$^4$ cells/mL) | 359 | 173 | 58 | 3 | 0.6 | Nt |
| Causative microorganisms | Gram positive bacillus | | | | | | |

In this case, the measured "degree of coagulation of the milk" and "judgment by pH of the milk" according to modified CMT methods (referred to as "measured CMT" hereafter) as a diagnostic marker of mastitis, and the measured "number of the somatic cells" were rapidly improved after the administration of glycyrrhizin. Disease conditions also disappeared 2 days after administration, and recovered enough for distribution of the milk 4 days after administration.

TABLE 2

Results of Example 2

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | − | − | − | − | − | − |
| | Aggregates in the milk | ± | − | − | − | − | − |
| Test of the milk | Degree of coagulation of the milk (modified CMT method) | ++ | + | − | − | − | − |
| | Judgment by pH of the milk (modified CMT method) | − | − | − | − | − | − |
| | Number of somatic cells in the milk (SCC × 10$^4$ cells/mL) | 202 | 7 | 5 | 9 | 42 | 40 |
| | Number of granulocytes in the milk (PMN × 10$^4$ cells/mL) | 96 | 2 | 0.6 | Nt | 24 | Nt |
| Causative microorganisms | Coagulase negative *Staphylococcus aureus* (hemolytic) | | | | | | |

Gram positive bacillus

Although the disease conditions are not so evident in this case as in Example 1, the measured CMT as a diagnostic marker of mastitis and the increase in the number of the, somatic cells were serious. However, the decrease of these values was observed in the early stages of one administration of glycyrrhizin. The condition was recovered to an extent enough for the distribution of the milk 3 days after administration.

TABLE 3

Results of Example 3

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | ++ | − | − | − | − | − |
| | Aggregates in the milk | + | + | − | − | − | − |
| Test of the milk | Degree of coagulation of the milk (modified CMT method) | +++ | − | ± | − | − | − |
| | Judgment by pH of the milk (modified CMT method) | + | − | − | − | − | − |
| | Number of somatic cells in the milk (SCC × 10$^4$ cells/mL) | 518 | 1061 | 143 | 75 | 68 | 8 |
| | Number of granulocytes in the milk (PMN × 10$^4$ cells/mL) | 346 | 359 | 66 | 39 | 38 | 5 |

TABLE 3-continued

Results of Example 3

| | | Days after the start of treatment | | | | | |
|---|---|---|---|---|---|---|---|
| | | Day 0 | Day 1 | Day 2 | Day 7 | Day 14 | Day 21 |
| Causative micro-organisms | Gram positive bacillus Coagulase negative *Staphylococcus aureus* | | | | | | |

The measured CMT and disease conditions were improved in the early stages of this case. Although the number of the somatic cells was high as compared with those of Examples 1 and 2, it was recovered enough for distribution on day 5 following administration.

TABLE 4

Results of Example 4

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | + | + | – | – | – | – |
| | Aggregates in the milk | ++ | + | – | – | – | – |
| Test of the milk | Degree of coagulation of the milk (modified CMT method) | + | + | ± | – | – | – |
| | Judgment by pH of the milk (modified CMT method) | ± | ± | – | – | – | – |
| | Number of somatic cells in the milk (SCC × 10$^4$ cells/mL) | 326 | 60 | 40 | 15 | 14 | 55 |
| | Number of granulocytes in the milk (PMN × 10$^4$ cells/mL) | 314 | 27 | 4 | 9 | ND | Nt |
| Causative micro-organisms | Gram-positive bacillus | | | | | | |

An improvement in the number of the somatic cells was evident in this case. The disease conditions and measured CMT were also improved at on the early stage of administration, and recovered to an extent enough for distribution 2 days after administration.

TABLE 5

Results of Example 5

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | + | – | – | – | – | – |
| | Aggregates in the milk | ++ | ++ | ± | – | – | – |

TABLE 5-continued

Results of Example 5

| | | Days after the start of treatment | | | | | |
|---|---|---|---|---|---|---|---|
| | | Day 0 | Day 1 | Day 2 | Day 7 | Day 14 | Day 21 |
| Test of the milk | Degree of coagulation of the milk (modified CMT method) | ± | ± | – | – | – | – |
| | Judgment by pH of the milk (modified CMT method) | – | – | – | – | – | – |
| | Number of somatic cells in the milk (SCC × 10$^4$ cells/mL) | 1298 | 376 | 251 | 74 | 35 | Nt |
| | Number of granulocytes in the milk (PMN × 10$^4$ cells/mL) | 1060 | 121 | 17 | 6 | 29 | Nt |
| Causative micro-organisms | Coagulase positive *Staphylococcus aureus* and hemolytic Gram positive bacillus | | | | | | |

The number of the somatic cells on the day of administration the highest-in this example. However, the number of the somatic cells and the disease condition recovered to a extent enough for distribution 7 days after administration of glycyrrhizin.

TABLE 6

Results of Example 6

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | ++ | ± | – | – | – | – |
| | Aggregates in the milk | + | – | – | – | – | – |
| Test of the milk | Degree of coagulation of the milk (modified CMT method) | ± | – | – | – | – | – |
| | Judgment by pH of the milk (modified CMT method) | – | – | – | – | – | – |
| | Number of somatic cells in the milk (SCC × 10$^4$ cells/mL) | 197 | 171 | 85 | 129 | 10 | 5 |
| | number of granulocytes in the milk (PMN × 10$^4$ cells/mL) | 189 | 89 | 2 | 6 | 0.1 | 0.05 |
| Causative micro-organisms | Coagulase positive *Staphylococcus aureus* and Gram positive bacillus | | | | | | |

The improvement of the disease conditions of mastitis was evident in this case. Although the number of the milk secretion cells showed a tendency to decrease after the initial administration, it increased slightly after the second administration (on day 7 from the start of the test). Further, the disease conditions recovered to an extent enough for distribution on day 14.

TABLE 7

Results of Example 7

| | | Days after the start of treatment | | | | | |
|---|---|---|---|---|---|---|---|
| | | Day 0 | Day 1 | Day 2 | Day 7 | Day 14 | Day 21 |
| Clinical diagnosis | Inflation and rigidity of the mamma | ++ | + | ± | – | – | – |
| | Aggregates in the milk | ++ | – | – | – | + | – |
| Test of the milk | Degree of coagulation of the milk (modified CMT method) | ++ | ± | ± | – | ++ | – |
| | Judgment by pH of the milk (modified CMT method) | ± | – | – | – | – | – |
| | Number of somatic cells in the milk (SCC × 10$^4$ cells/mL) | 499 | 1080 | 673 | 459 | 700 | 45 |
| | Number of granulocytes in the milk (PMN × 10$^4$ cells/mL) | Nt | Nt | Nt | Nt | Nt | Nt |
| Causative microorganisms | Coagulase positive *Staphylococcus aureus* and hemolylic Gram positive bacillus | | | | | | |

Both the disease conditions and the results of the test of the milk were remarkably improved on day 2 to 3 after the administration of glycyrrhizin in all cases. Distribution of the milk was possible 2 to 5 days after a dose in Examples 1 to 5, or at the latest 7 days after treatment began. The disease conditions recovered to an extent enough for distribution within 14 to 22 days, in the examples with two administrations of dos 8.

The observed scores of "degree of coagulation of the milk" based on the modified CMT method, in the seven examples of administration of GL to the mastitis-manifesting mammae, i.e. Examples 1 to 7, are summarized in Table 8.

TABLE 8

Example of administration of GL

| | | Days after the start of treatment | | |
|---|---|---|---|---|
| | Example | Day 0 | Day 2 or 3 | Day 21 |
| Milk test I: Degree of coagulation of milk (Modified CMT method) | 1 | ++ | ± | – |
| | 2 | ++ | – | – |
| | 3 | +++ | ± | – |
| | 4 | + | ± | – |
| | 5 | ± | – | – |
| | 6 | ± | – | – |
| | 7 | ++ | ± | – |

Cows manifesting clinical type mastitis were treated with antibiotics mainly comprising Sephazon formulations as a comparative drug in the six cases of treatment of the Holstein milk secreting cows shown in Comparative examples 1 to 6 below. The observed results of "degree of coagulation of the milk" in the Comparative Examples 1 to 6 are shown in Table 9.

COMPARATIVE EXAMPLES 1 to 6

Nine g of an antibiotic (trade name: Cefamedin S sold by Fijisawa Pharmaceutical Industries Co., containing 450 mg (titer) of Cefazolin in 9 g of cefamedin) were administered to the mammae of six cows using the same method as in Examples 1–5. The degree of coagulation of the milk was tested by the modified CMT method as in Examples 1 to 5.

TABLE 9

Comparative Examples of administration of antibiotics

| | Comparative Example | Days after the start of treatment | | |
|---|---|---|---|---|
| | | Day 0 | Day 2 or 3 | Day 21 |
| Milk test I: degree of coagulation of milk | 1 | ++ | ++ | ++ |
| | 2 | +++ | +++ | +++ |
| | 3 | +++ | ++ | ++ |
| | 4 | ++ | ++ | +++* |
| | 5 | ++ | ++ | – |
| | 6 | +++ | +++ | – |

*Milking was stopped and the obtained milk was disposed of, because mastitis became worse.

The degree of coagulation of the milk deceased in all seven cases of the GL administration group, and the coagulation was not found by day 21 in all cases. In contrast, although two of the six cases of the antibiotic treated comparative group on day 21 after the start of treatment, no improvement was observed in the remaining four cases.

It should be understood that the foregoing relates to only a preferred embodiment of the invention, and it is intended to cover all changes and modifications of the examples of the invention herein chosen for the purposes of the disclosure, which do not constitute departures from the sprit and scope of the invention.

What is claimed is:

1. A therapeutic agent for treatment of mastitis in cattle consisting essentially of glycyrrhizin or pharmaceutically acceptable salts thereof as effective ingredients in an amount adjusted to administer from approximately 400 to approximately 800 mg per mamma, and a pharmaceutically acceptable carrier, wherein the therapeutic agent is directly administered into mammae of the cattle.

2. A therapeutic method for treatment of mastitis in cattle, comprising administering a therapeutic agent consisting essentially of glycyrrhizin or pharmaceutically acceptable salts thereof, as effective ingredients in an amount adjusted to administer from approximately 400 to approximately 800 mg per mamma and a pharmaceutically acceptable carrier to mamma of the cattle.

3. The therapeutic method for treatment of mastitis in cattle according to claim 2, wherein glycyrrhizin or pharmaceutic ally acceptable salts thereof are administered by direct injection using a cannula.

4. A therapeutic agent for treatment of mastitis in cattle consisting essentially of glycyrrhizin or pharmaceutically acceptable salts thereof as effective ingredients in an amount adjusted to achieve from approximately 0.08 to approximately 0.4 mg/ml of the effective ingredients in milk of the cattle, and a pharmaceutically acceptable carrier.

5. A therapeutic agent for treatment of mastitis in cattle consisting essentially of glycyrrhizin or pharmaceutically acceptable salts thereof as effective ingredients and a pharmaceutically acceptable carrier wherein a dosage unit of the therapeutic agent comprises from approximately 400 mg to approximately 800 mg of the effective ingredients.

6. The method of claim 2 wherein glycyrrhizin or pharmaceutically acceptable salts thereof are administered in an amount to achieve from approximately 0.08 to approximately 0.4 mg/ml of glycyrrhizin or pharmaceutically acceptable salts thereof in milk of the cattle.

7. The method of claim 2, wherein a dosage unit of the therapeutic agent comprises from approximately 400 mg to approximately 800 mg of glycyrrhizin or pharmaceutically acceptable salts thereof.

* * * * *

UNITED STATES PATENT AND TRADEMARK OFFICE
CERTIFICATE OF CORRECTION

PATENT NO. : 6,872,709 B2
DATED : March 29, 2005
INVENTOR(S) : Katsuo Kumagai

It is certified that error appears in the above-identified patent and that said Letters Patent is hereby corrected as shown below:

<u>Title page,</u>
Item [73], Assignee, should be -- Kyoritsu Seiyaku Corporation, Tokyo (JP) and T-Cell Research Institute, Miyagi-Ken (JP) --

Signed and Sealed this

Twelfth Day of July, 2005

JON W. DUDAS
*Director of the United States Patent and Trademark Office*